United States Patent
Hirayama

[11] Patent Number: 6,048,499
[45] Date of Patent: Apr. 11, 2000

[54] ANTISEPTIC CLEAN SYSTEM

[75] Inventor: Shoji Hirayama, Yamato, Japan

[73] Assignee: Hirayma Setsube Kabushiki Kaisha, Kanagawa-Ken, Japan

[21] Appl. No.: 08/883,350

[22] Filed: Jun. 26, 1997

Related U.S. Application Data

[63] Continuation of application No. 08/386,490, Feb. 10, 1995, abandoned.

[51] Int. Cl.⁷ .................................................... A61L 9/18
[52] U.S. Cl. ......................... 422/121; 422/122; 454/187; 55/385.2; 55/524; 96/224; 96/226
[58] Field of Search ................................ 422/122, 4, 5, 422/121; 454/187; 55/385.2, 467.1, 524; 96/224, 226, FOR 175

[56] References Cited

U.S. PATENT DOCUMENTS

| | | | |
|---|---|---|---|
| 4,780,333 | 10/1988 | Smith et al. | 427/236 |
| 4,788,038 | 11/1988 | Matsunaga | 422/22 |
| 5,256,105 | 10/1993 | Austin | 454/187 |
| 5,449,443 | 9/1995 | Jacoby et al. | 204/157.3 |
| 5,529,807 | 6/1996 | Burkhart, Jr. et al. | 427/372.2 |
| 5,564,065 | 10/1996 | Fleck et al. | 422/186.3 |

FOREIGN PATENT DOCUMENTS

| | | |
|---|---|---|
| 63-80833 | 4/1988 | Japan . |
| 2-207824 | 8/1990 | Japan . |
| 3-106420 | 5/1991 | Japan . |

*Primary Examiner*—Elizabeth McKane
*Attorney, Agent, or Firm*—Stevens, Davis, Miller & Mosher, L.L.P.

[57] ABSTRACT

An antiseptic clean system according to the invention is designed to effectively and thoroughly destruct not only drifting microbes but also germs that have fallen and are adhering to the panels and to the backsides and the gaps of the pieces of equipment installed in the room. It is adapted for use with a clean room provided with antiseptic panels and comprises one or more than one air conditioners, each having an air conditioner main body containing therein a photocatalyst so that air is fed back into the room after passing through the photocatalyst.

5 Claims, 5 Drawing Sheets

ANTISEPTIC CLEAN SYSTEM

This is a Rule 60 Continuation of application Ser. No. 08/386,490 filed Feb. 10, 1995, now abandoned.

BACKGROUND OF THE INVENTION

1. Field of the Invention

This invention relates to an antiseptic clean system adapted to destruct germs and other microorganisms brought into a room both by the room itself and by means of an air conditioner installed in the room.

2. Prior Art

Conventional techniques employed in clean systems comprising an air conditioner include arranging a germicidal lamp within the air conditioner main body to destruct germs adhering to the filter of the air conditioner or drifting in the air and/or inhibit the reproduction of germs within the system and utilizing antiseptic filters made of one or more than one antiseptic materials, which are a relatively new technological development. While these techniques are effective to a certain extent against germs of various types, viruses can easily pass through the filter and be blown into the room where the air conditioner is installed so that clean systems employing such techniques are not satisfactorily suited for air conditioners to be installed in operating rooms (clean rooms) in hospitals because of the poor sterilizing effect of the techniques.

This will be described in greater detail by referring to FIG. 6 of the accompanying drawings.

FIG. 6 shows part of a clean room of a known type in lateral cross section, employing a so-called type clean system and comprising one or more than one air cleaners installed within the room that do not require a duct system which is normally provided with a number of ducts having a large cross section and arranged under the ceiling or the floor of the room. Thus, such a line type clean system is advantageous in that it does not occupy a large space within the room.

The clean room 1 comprises walls, a ceiling and a floor made of materials that produce little or no dirt and any gaps that may be found within the room are sealed by means of a sealing material containing silicon so that the room may be held under a hermetically sealed condition.

One or more than one air cleaners 2 are arranged on some of the walls of the room 1 and each of the air cleaners 2 comprises a prefilter 20 and a filter 21 designed to trap dirt and microorganisms passing therethrough. Each air cleaner 2 also comprises a fan 22 for forcibly circulating air within the room and an air conditioner 23.

In FIG. 6, arrows indicate how air circulates within the room 1. Air that can contain dirt is taken into the air cleaners 2 arranged within the room 2 through the bottoms thereof so that dirt are mostly caught by the prefilters 20. Thereafter, air is cleaned as it passes through the air conditioners 23, the fans 22 and the filters 21 before it is returned into the room 1 through a clean air feed unit 24 arranged under the ceiling.

The filters can catch drifting microorganisms including pathogenic microbes, fungi, spores and eumycetes. On the other hand, microorganism that have fallen onto the panels of the system are killed by germicidal lamps or ozone.

Of clean rooms of the above described type, so-called bio-clean rooms have a particularly rigorous control system against germs for keeping the room under control for cleanness by regularly counting the number of fallen microorganisms and cleansing the inside of the room 1.

Problems to be solved by the invention

Dirt that are brought into a clean room by way of human bodies and pieces of equipment can be satisfactorily removed by the prefilters and the filters of a line type clean system.

However, microorganisms cannot be wiped out by such a system.

With a sterilizing system of the above described type comprising filters, germs can be reproduced and multiplied on the rear side of the filter and then turned back into the room way of the air cleaners.

Filters haveing a sterilizing effect may be used for such a system in order to eliminate the above problem. However, filters cannot satisfactorily kill germs adhering to the filters and the backsides and the gaps of the pieces of equipment installed in the room.

Additionally, the technique of sterilizing and cleansing the inside of a room as described above is costly and cumbersome and sterilizers used with such a technique is harmful to the human body and take considerable time until they become effective. This means that, once the room that may be an operating room is sterilized and cleansed with such a technique, it needs to be kept off limits for a given period of time. Still additionally, the operation of sterilization and cleansing needs to be perodically repeated in order to constantly keep the room clean, be it an operating room or not, making the entire operation rather costly.

In view of the above technological problems, it is therefore an object of the invention to provide a clean system that can sterilize germs and other microorganisms brought into a room in a simple manner on a stable basis for a long perod of time without using the operation of sterilization and cleansing.

SUMMARY OF THE INVENTION

According to the invention, the above object is achieved by providing an antiseptic clean system adapted for use in a clean room comprising panels for sealing the room that produce little or no dirts and air cleaners and air conditioners for removing dirts within the room, characterized in that at least some of said panels are panels having an antiseptic effect (hereinafter referred to as antiseptic panels). An antiseptic panel that can advantageously be used for the purpose of the present invention is formed by applying ceramic granules carrying thereon powder of a metal having an antiseptic effect (hereinafter referred to as antiseptic metal) onto an ordinary panel or applying a carrier member impregnated with ceramic granules carrying thereon powder of an antiseptic metal to an ordinary panel.

Each of the air conditioners comprises therein a heat exchanger, a fan and a number of filters and either the most upstream or the most downstream one of the filters carries thereon a photocatalyst which is so arranged as to be irradiated with rays of light so that air drawn into the air conditioner through its air inlet port passes through the photocatalyst before it is blown out of its air outlet port.

Said photocatalyst consists of granules of titanium oxide, cadmium cerite or strontium titanate or a filter formed by impregnating a piece of unwoven fabric with one of the above compounds.

(Function)

Since an antiseptic clean system according to the invention comprises antiseptic panels to be used for the room where it is installed, it can effectively and thoroughly destruct not only drifting microbes but also germs that have fallen and are adhering to the panels and to the backsides and the gaps of the pieces of equipment installed in the room.

Antiseptic panels that can advantageously be used for the purpose of the present invention include those formed by applying ceramic granules made of silica, alumina or zirconia or a mixture thereof carrying thereon powder of an antiseptic metal such as Ag, Au, Pt, Cu or Ni or an alloy or mixture of any of them as a coating material, those formed by impregnating carriers in the form of sheets of woven or unwoven fabric with such granules as described above to form thin films and applying them to the surface of ordinary panels, those formed by coating granules of a porous ceramic material such as a foaming ceramic material having a three-dimensional network structure with an antiseptic metal and applying coated granules to the surface of ordinary panels and those formed by preparing sheets of a porous and antiseptic metal such as foaming antiseptic metal having a three-dimensional network structure and applying them to the surface of ordinary panels.

The antiseptic metal on the surface of an antiseptic panel of the above described type operates as a catalyst that activates oxygen contained in circulating air, which by turn destructs not only drifting microbes but also germs that have fallen and are adhering to the panels and to the backsides and the gaps of the pieces of equipment installed in the room through oxidization and chemical decomposition.

A photocatalyst to be used for the purpose of the present invention is made of titaniumoxide, cadmium cerite or strontium titanate and, when irradiated with rays of light, shows a strong oxidizing and reducing effect on the surface of destruct microbes.

Such a photocatalyst consists of granules of titanium oxide, cadmium cerite or strontium tinanate or a filter formed by impregnating a piece of unwoven fabric with one of the above compounds.

An air conditioner to be used for the purpose of the present ivention comprises a main body containing therein a number of filters and either the most upstream or the most downstream one of the filters carries thereon a photocatalyst of the above described type which is so arranged as to be irradiated with rays of light so that air drawn into the air conditioner through its air inlet port passes through the photocatalyst before it is blown out of its air outlet port. With such an arrangement, microorganisms including viruses can be effectively destructed and/or inhibited from reproduction within the air conditioner main body having a simple configuration.

Now, the present invention will be described in greater detail by referring to FIGS. 1 through 5 of the accompanying drawings that illustrate a preferred embodiment of the invention.

DETAILED DESCRIPTION OF THE PREFERRED EMBODIMENT

Figure 1:
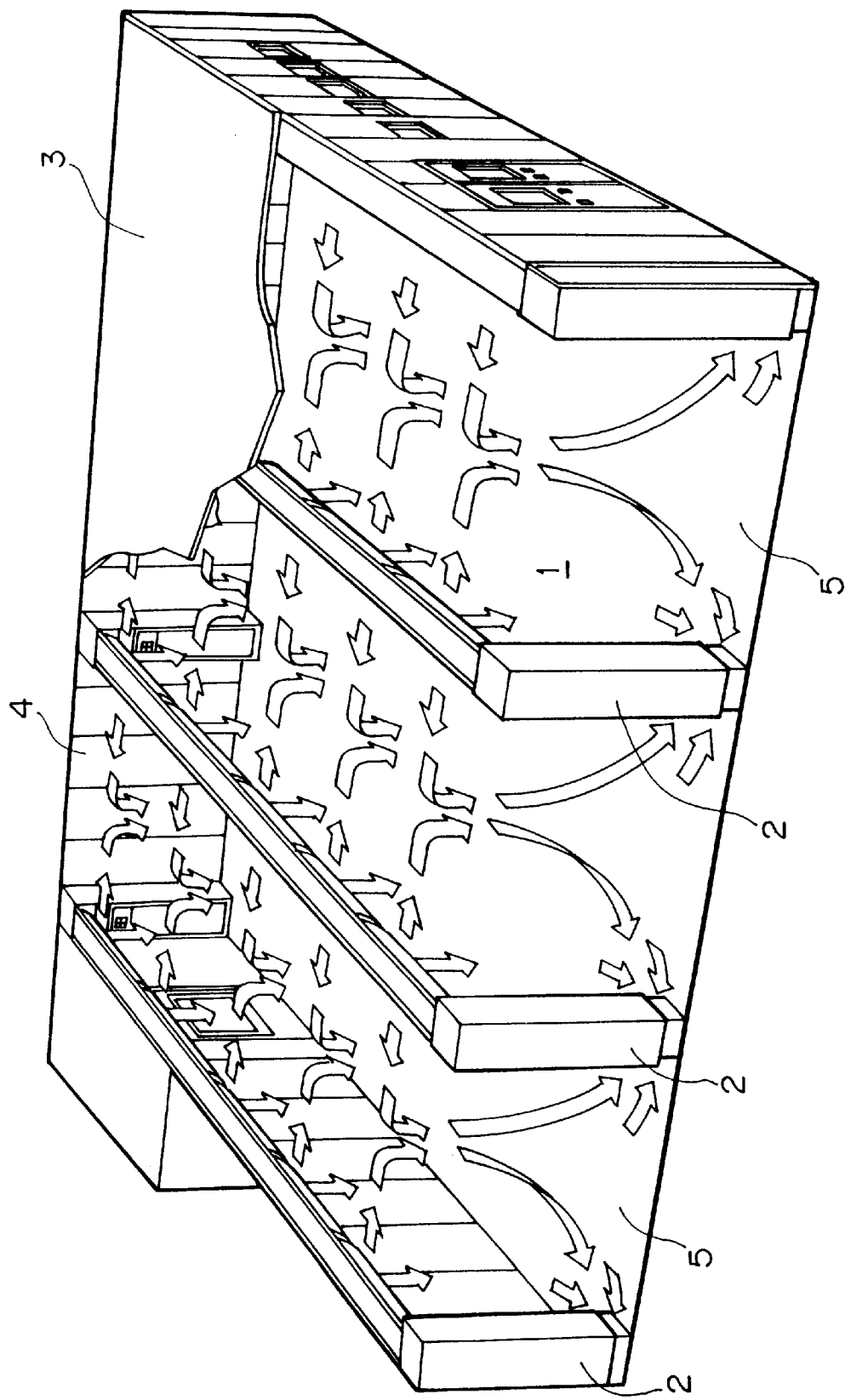
FIG. 1 is a partially torn off schematic perspective view of a room provided with an embodiment of antiseptic clean system according to the invention.

FIG. 1 shows a partially torn off schematic perspective view of a room where an embodiment of antiseptic clean system according to the invention is installed. The system is of a so-called line type.

Referring to FIG. 1, the room 1 is provided on a wall thereof with an air conditioner main body 2 comprising a prefilter, a fan and a number of filters and under the ceiling 3 thereof with air outlet ports held in communication with the main body 2 in order to blow out air cleaned and sterilized by the main body 2.

In FIG. 1, reference numerals 4 and 5 respectively denotes the walls and the floor of the room. The walls 4, the floor 5 and the ceiling 3 are made of antiseptic materials.

Figure 2:
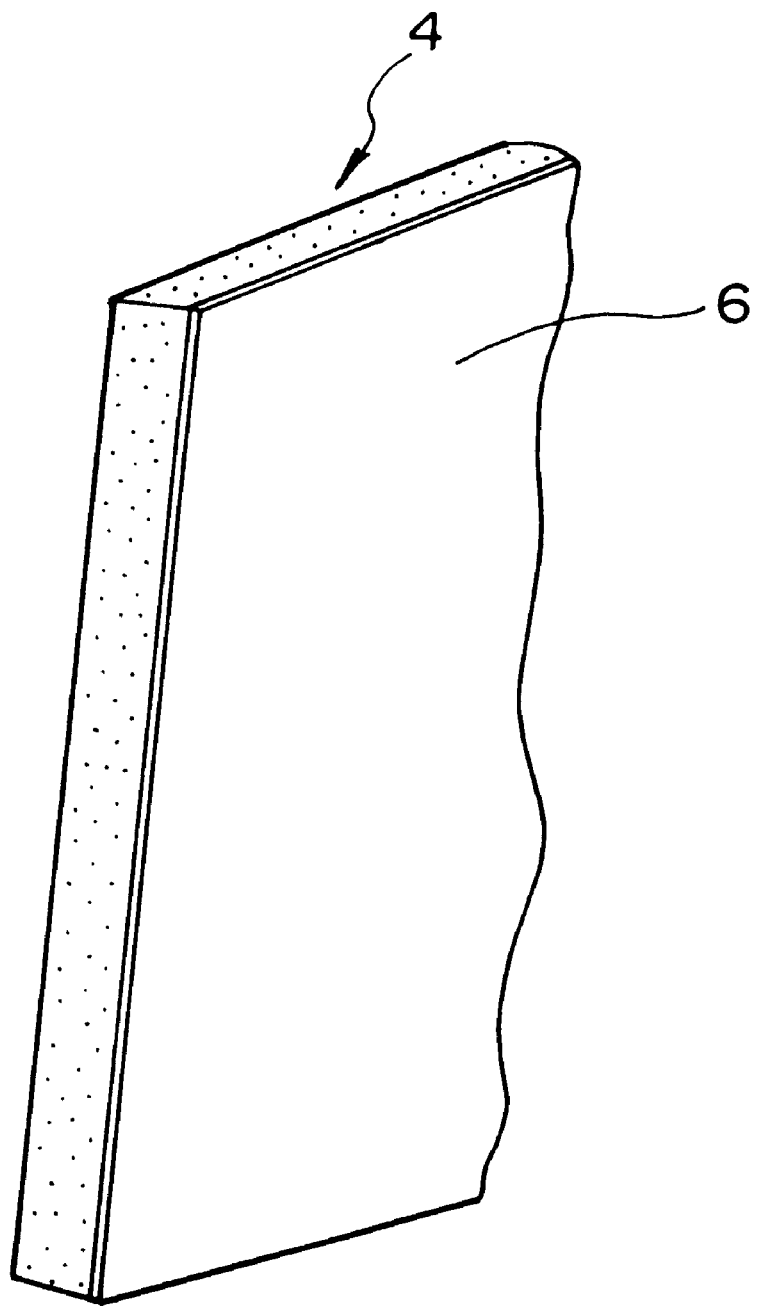
FIG. 2 is a schematic partial view of a wall to be used for the embodiment of antiseptic clean system of FIG. 1.

FIG. 2 is a schematic partial view of a wall used for the embodiment of antiseptic clean system of FIG. 1. The wall 4 has a coat of fabric 6 impregnated to a thickness of 0.05 to 0.5 microns (and a BET specific surface area of 300 to 600 $m^3/g$) with fine particles of a silica-alumina type ceramic material having an average particle size of 0.2 micron, each coated with an antiseptic powdered mixture of Ag and Cu.

In a clean room having a configuration as described above, while the air conditioner traps dirts brough into the room by human bodies and goods, the antiseptic walls 4, floor 5 and ceiling 3 effectively kill fallen microbes and germs adhering to the rearsides and the gaps of the pieces of equipment within the room.

Note that the particle size, the film thickness and the BET specific surface area are not limited to the above cited values but subject to changes depending on the dimensions of the room and other parameters. An antiseptic coat may be applied to a wall with paint.

Figure 3:
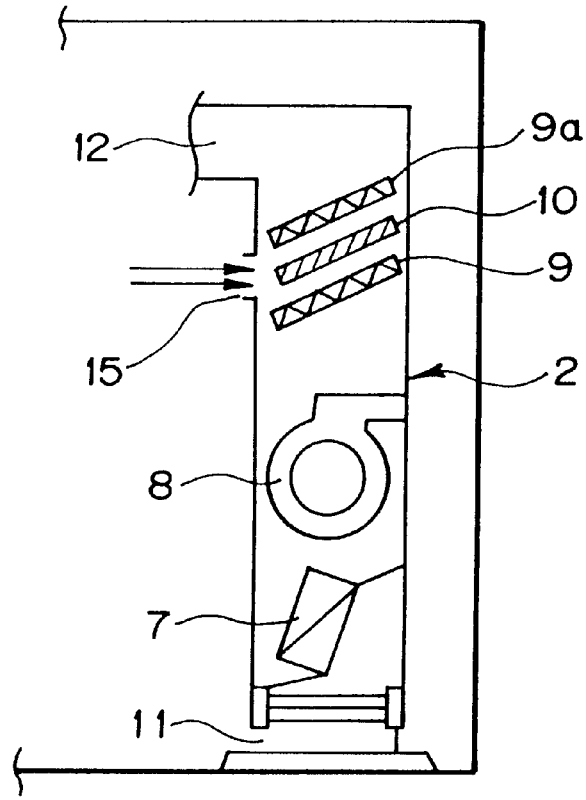
FIG. 3 is a schematic sectional side view of an air conditioner main body to be used for the embodiment of antiseptic clean system of FIG. 1.

FIG. 3 is a schematic sectional side view of an air conditioner main body to be used for the embodiment of antiseptic clean system of FIG. 1. The air conditioner main body 2 comprises a heat exchanger 7, an air take-in fan 8, a filter 9, a photocatalyst 10 and a filter 9a arranged in the mentioned order from the bottom toward the top between an air inlet port 11 near the lower end and an air outlet port 12 near the upper end of the main body.

The photocatalyst 10 consists of granules of titanium oxide, cadmium cerite or strontium titanate filled in a column 13.

Figure 4:
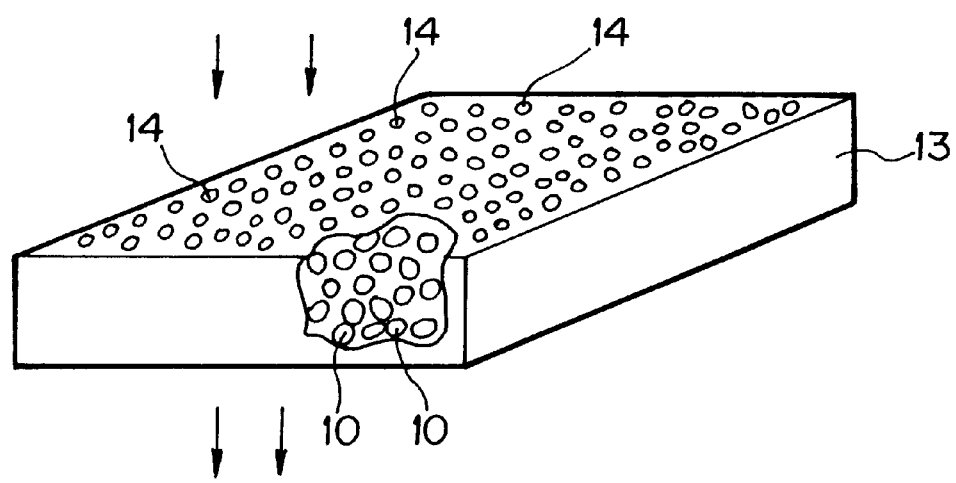
FIG. 4 is a partially torn off schematic perspective view of a photocatalyst to be used for the embodiment of antiseptic clean system of FIG. 1.
Figure 5A:
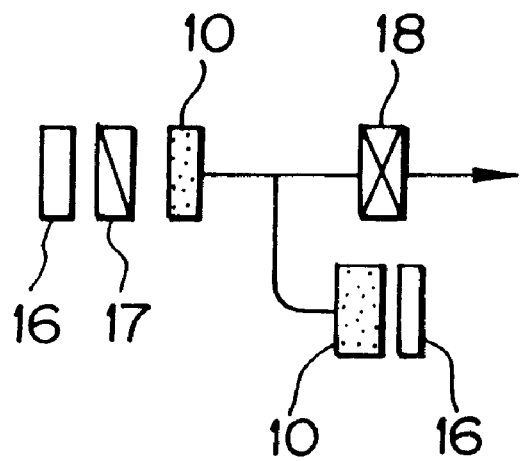
FIGS. 5A–5D are a schematic illustration showing possible alternative arrangements of a photocatalyst and filters to be used for the embodiment of antiseptic clean system of FIG. 1.
Figure 5C:
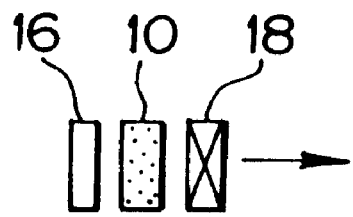
Figure 5B:
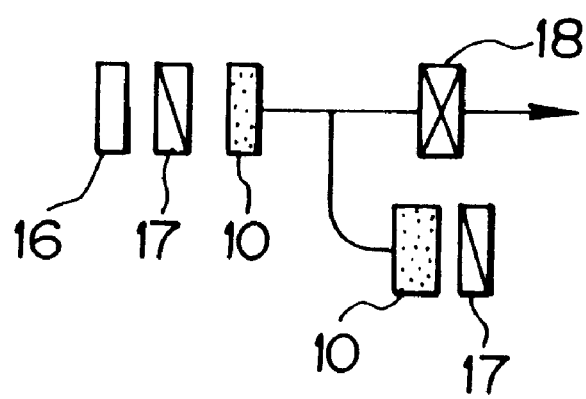
Figure 5D:
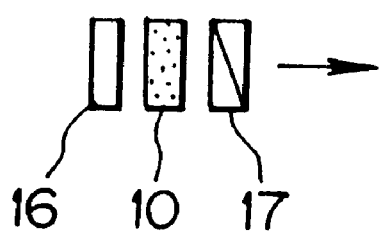
Figure 6:
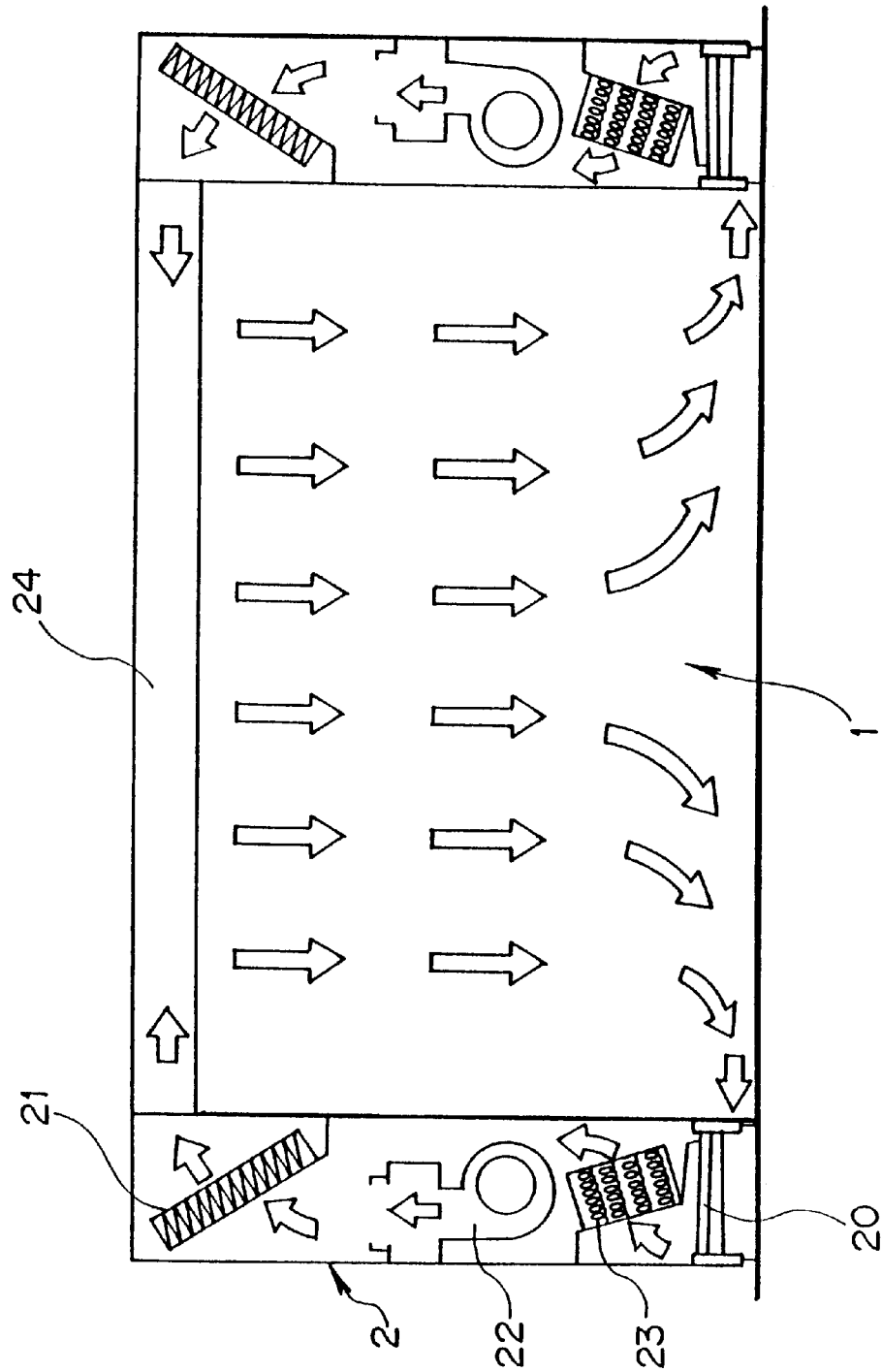
FIG. 6 is a partially torn off schematic perspective view of a room provided with a conventional clean system.

As shown in FIG. 4, the column 13 is hollow and made of a transparent material such as acrylic resin. The column has a large number of pores 14 on the inner surface, each having a diameter smaller than the average size of 3 to 5 mm of the granules of the photocatalyst.

The photocatalyst 10 may alternatively be a filter prepared by impregnating a sheet of unwoven fabric with titanium oxide, cadmium cerite or strontium titanate. Still alternatively, it may be formed by simply applying one of the compounds to a sheet of unwoven fabric.

If the photocatalyst 10 is realized in the form of a filter, a column 13 is not required and it may be arranged between the filters 9 and 9a by itself.

The air conditioner main body 2 is provided with an optical guide 15 for introducing light into the main body 2 by way of appropriate means such as optical fiber in order to irradiate the photocatalyst 10 with rays of light. Alternatively, portions of the main body 2 located close to the photocatalyst 10 may be made of a transparent material such as glass or acrylic resin so that the photocatalyst 10 may be irradiated with rays of light transmitted into the main body 1 through the transparent material.

FIG. 5 is an schematic illustration showing four possible alternative arrangements (A), (B), (C) and (D) of the photocatalyst 10 and the filters 9, 9a. It is particularly advantageous to arrange a prefilter 10 or a middle efficiency filter 17 upstream relative to the photocatalyst 10 and an ultra low penetration air-filter (ULPA) 18 downstream relative to the photocatalyst 10. With such an arrangement, germs of various types and dirts are mostly removed by the prefilter or middle efficiency filter and viruses and microbes that have passed through it are killed by the photocatalyst before air is completely and thoroughly cleaned by the ULPA filter so that the ULPA filter which is costly may be kept free from clogging and other troubles for a prolonged period of time. The use of a prefilter or middle efficiency filter arranged upstream relative to the photocatalyst by turn protects the latter against clogging so that it may enjoy a prolonged service life.

By subjecting the inner walls of the air conditioner main body, the fan, the filters, the heat exchanger and other components to an antiseptic process as described above, the entire system can be made to show an improved antiseptic effect.

(Advantages of the invention)

As described above in detail, an antiseptic clean system according to the invention can produce a highly sterilized clean room without requiring any particular operation of sterilization and cleansing. Additionally, it is harmless to the human body and can maintain its effect for a long time on a stable basis.

Finally, by arranging a photocatalyst between a pair of filters within the air conditioner of a clean system according to the invention and irradiating it with rays of light, not only ordinary dirts can be effectively removed but also germs of various types including viruses can be destructed and any possible reproduction thereof can be inhibited in an effective manner in order to supply the room with truly clean air.

What is claimed is:

1. An antiseptic clean system adapted for use in a clean room, which clean room comprises panels for at least one of the walls, ceiling and floor with any gaps between said walls, ceiling and floor being sealed with a sealing material, said panels having an antiseptic effect characterized in that said clean system comprises an air conditioner containing therein a heat exchanger, a fan, filters, a light guide for introducing a source of light, and a photocatalyst arranged upstream or downstream of one of the filters in such a way that it is irradiated with rays of light from said light guide so that air drawn into the air conditioner main body through an air inlet port is made to pass through the photocatalyst and blown into the room through an air outlet port, wherein an antimicrobial agent is provided on at least one of said filters, heat exchanger, fan, air inlet port and air outlet port.

2. An antiseptic clean system according to claim 1, characterized in that said photocatalyst consists of granules of titanium oxide, cadmium cerite or strontium titanate.

3. An antiseptic clean system according to claim 1, wherein said air inlet port is at a lower end of said air conditioner and said air outlet port is near an upper end of said air conditioner, such that air is sucked into the air conditioner from a lower part of said clean room and blown into said clean room at a level above said lower part, thereby imparting a circulation effect within said clean room.

4. An antiseptic clean system according to claim 1, wherein said air conditioner further comprises an air duct connected to at least one of said air inlet and air outlet port, the duct being provided on an inner wall with an antimicrobial agent.

5. An antiseptic clean system adapted for use in a clean room, which clean room comprises panels for at least one of the walls, ceiling and floor with any gaps between said walls, ceiling and floor being sealed with a sealing material, said panels having an antiseptic effect characterized in that said clean system comprises an air conditioner containing therein a heat exchanger, a fan, filters, a light guide for introducing a source of light, and a photocatalyst arranged upstream or downstream of one of the filters in such a way that it is irradiated with rays of light from said light guide so that air drawn into the air conditioner main body through an air inlet port is made to pass through the photocatalyst and blown into the room through an air outlet port, wherein an antimicrobial agent is provided on at least one of said filters, heat exchanger, fan, air inlet port and air outlet port, said photocatalyst is a filter formed by impregnating a sheet of unwoven fabric with fine particles of titanium oxide, cadmium cerite or strontium titanate or applying fine particles of one of the above compounds to a sheet of unwoven fabric.

\* \* \* \* \*